United States Patent [19]
Kaplan et al.

[11] 3,933,150
[45] Jan. 20, 1976

[54] MEDICAL PNEUMATIC TROUSER FOR EMERGENCY AUTOTRANSFUSION

[75] Inventors: Burton H. Kaplan, Fort Leavenworth, Kans.; Forrest R. Poole; John E. Flagg, both of Worcester, Mass.

[73] Assignee: David Clark Company Incorporated, Worcester, Mass.

[22] Filed: Feb. 8, 1974

[21] Appl. No.: 440,644

[52] U.S. Cl.... 128/24 R; 128/DIG. 15; 128/DIG. 20
[51] Int. Cl.² ............................................. A61H 1/00
[58] Field of Search ...... 128/134, 133, 60, DIG. 20, 128/87 R, 89 R, 90, 24 R, DIG. 15

[56] References Cited
UNITED STATES PATENTS

| | | | |
|---|---|---|---|
| 1,608,239 | 11/1926 | Rosett | 128/60 |
| 2,699,165 | 1/1955 | Ferrier | 128/60 |
| 2,747,570 | 5/1956 | Jobst | 128/60 |
| 3,083,708 | 4/1963 | Gottfried | 128/39 |
| 3,218,103 | 11/1965 | Boyce | 297/384 |
| 3,224,415 | 12/1965 | Gottfried | 128/134 |
| 3,361,132 | 1/1968 | Rentsch | 128/134 |
| 3,465,749 | 9/1969 | Moreland et al. | 128/24 R |

*Primary Examiner*—Lawrence W. Trapp
*Attorney, Agent, or Firm*—Thompson, Birch, Gauthier & Samuels

[57] ABSTRACT

An apparatus for the treatment of a victim suffering from shock includes a single piece, double-walled panel of flexible material forming a chamber adapted to receive and contain a pressurized gas. The panel has a pair of lower sections adapted to surround the legs of the victim, and an upper section adapted to surround the abdomen of the victim in the region below the victim's rib cage. When the panel is inflated by the introduction of pressurized gas into the chamber, a pressure is exerted on the legs and abdomen of the victim, thereby decreasing the volume of venous blood pooled therein and producing an increased venous return to the victim's heart. This external pressure also provides immobilization for the victim and affords to him protection and comfort while being transported from an accident site to a medical facility.

5 Claims, 4 Drawing Figures

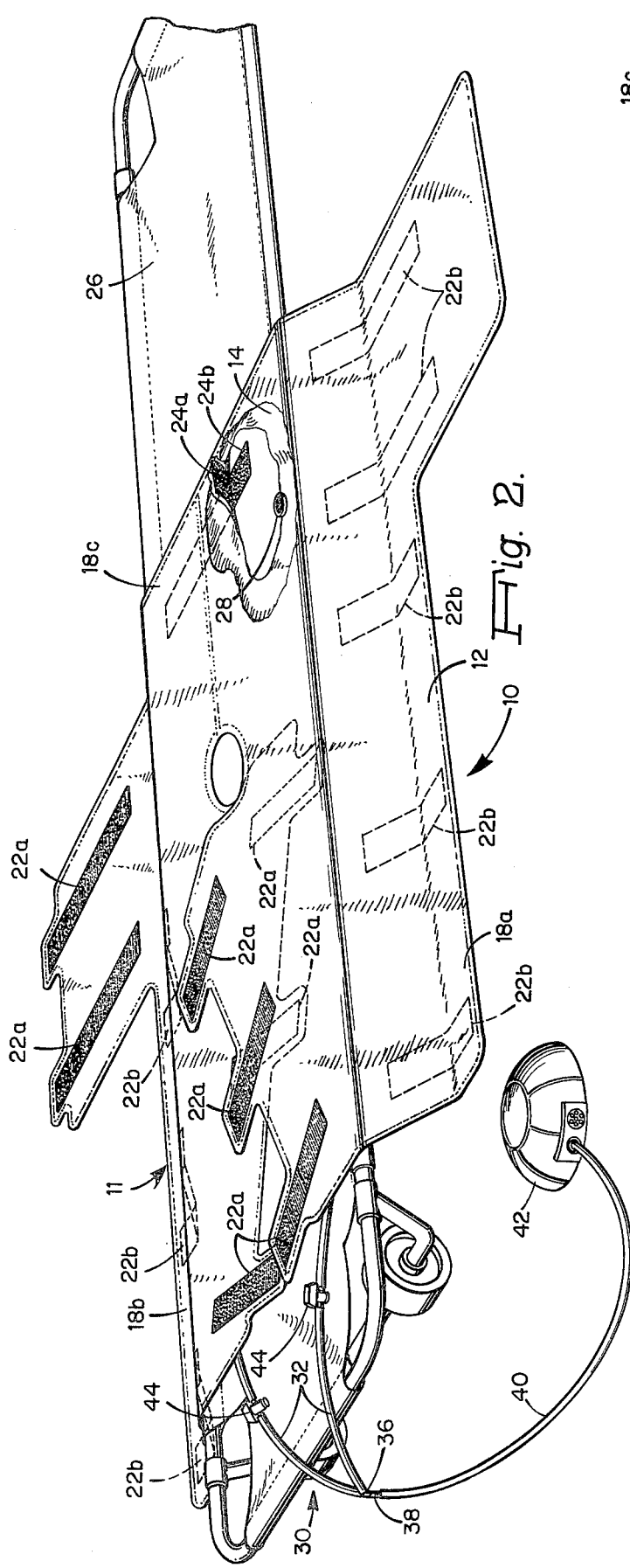
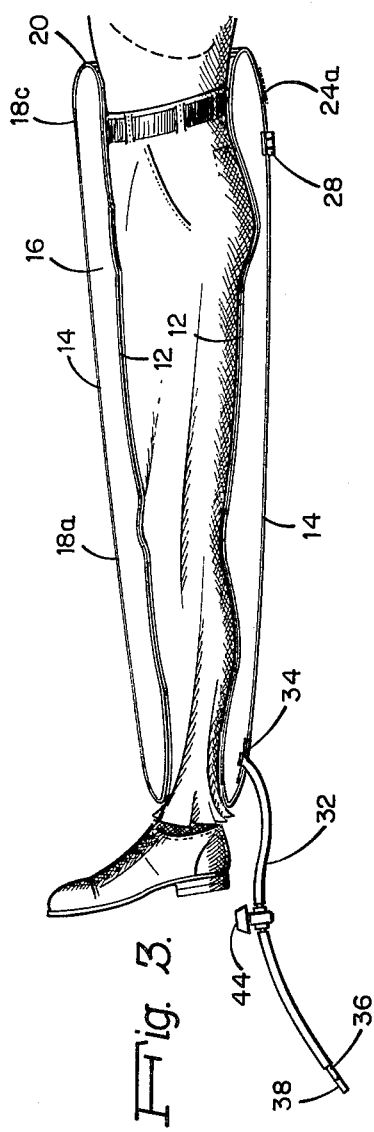

MEDICAL PNEUMATIC TROUSER FOR EMERGENCY AUTOTRANSFUSION

DESCRIPTION OF THE INVENTION

This invention relates generally to the emergency treatment of victims suffering from shock (hemorrhage or other), and in particular to a novel apparatus for transfusing the victim with his own stagnate blood.

Shock may be defined as a state of circulatory collapse, frequently associated with insufficient return of blood to the heart, and manifested by a persisting deficiency of blood flow to the peripheral tissues. The venous system becomes dilated, permitting blood to pool. Stagnation and clotting occur, and an insufficient amount of blood is returned to the heart. As this occurs, the body reacts by increasing the pulse rate, but without compensating for the insufficient return of blood to the heart. Arterial blood pressure thus decreases and the demise of the victim occurs unless treatment is initiated.

Emergency medical attendants, corpsmen, paramedical personnel and the like are taught five basic principles in the treatment of shock traumatized victims. These are:

1. Clear the airway.
2. Stop the bleeding.
3. Elevate the lower half of the body.
4. Administer intravenous fluids and medication.
5. Immobilization.

In addition to the above, counter pressure is sometimes applied to the victim's legs by wrapping the legs with elastic bandages in order to decrease the volume of venous blood trapped or pooled therein. However, this technique is time consuming and not adaptable to emergency situations. Moreover, paramedical personnel often do not carry blood for transfusion.

It is, accordingly, a general object of the present invention to provide a new and improved apparatus for augmenting the capability of paramedical personnel in the emergency treatment of victims in shock. To this end, the present invention provides an inflatable trouser-like garment which may be opened and laid flat to receive a victim, rapidly closed to surround the victim's legs and abdomen, and thereafter inflated to exert a pressure on the abdomen and legs to return venous blood pooled therein to the victim's heart.

A further object of the present invention is the provision of an apparatus which in addition to operating as an emergency autotranfusion means, also serves as a means of immobilizing the victim during transfer from an accident site to a medical facility.

These and other objects and advantages of the present invention will become more apparent as the description proceeds with the aid of the accompanying drawings, wherein:

FIG. 2 is a view in perspective, with portions broken away, of the apparatus shown in FIG. 1, in an open condition on a stretcher of conventional design;

FIG. 3 is a sectional view taken along lines 3—3 of FIG. 1; and,

Figure 1:
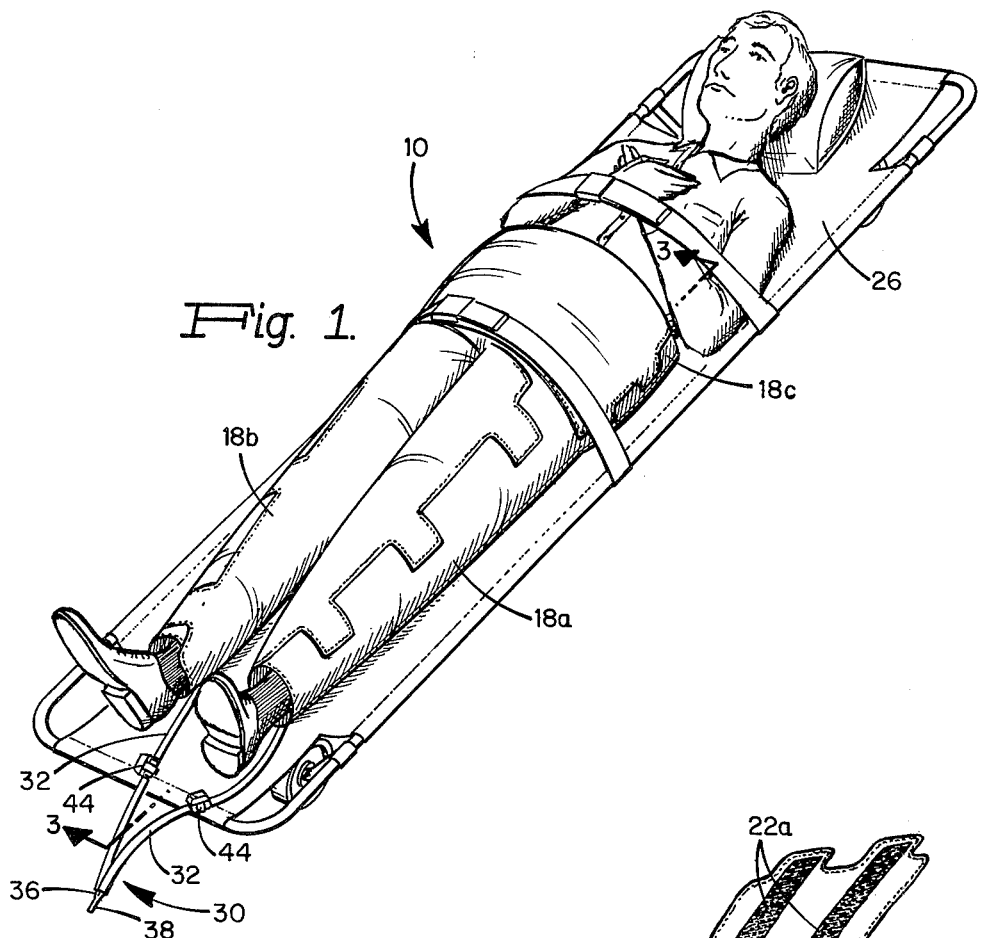
FIG. 1 is a view in perspective showing an apparatus embodying the concepts of the present invention applied to legs and abdomen of a victim's body.

Referring now to the drawings wherein like numbers designate the same parts throughout the several views, there is generally indicated at 10 a preferred embodiment of an apparatus in accordance with the present invention. As is best shown in FIG. 2, the apparatus includes a panel 11 having opposed walls 12 and 14 which are joined in sealing engagement about their peripheral edges to enclose a chamber 16. The walls 12 and 14 may be fabricated from any known flexible material, such as for example plastic, which is impervious to a gas such as air.

Figure 4:
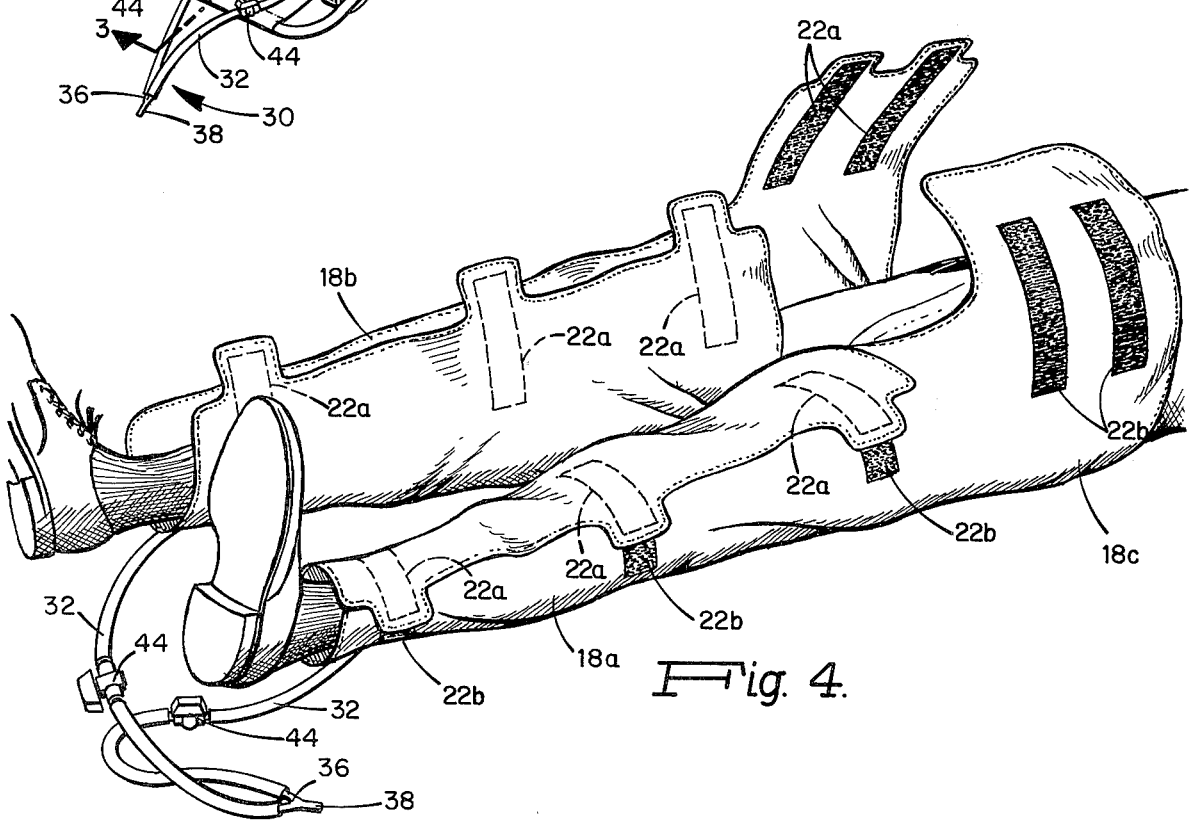
FIG. 4 is another perspective view showing the apparatus of FIGS. 1–3 during the application thereof to a victim's body.

The panel 11 includes a pair of lower sections 18a and 18b and an upper section 18c. As is best shown in FIG. 4, the lower sections 18a and 18b are adapted to be wrapped around a victim's legs, and the upper section 18c is likewise adapted to be wrapped around the victim's abdomen. The upper edge 20 (see FIG. 3) of upper section 18c is located beneath the victim's rib cage.

Fastening means are provided on the exterior surfaces of the panel 11 to hold the apparatus in its applied position on the victim's body. In the embodiment herein shown, the fastening means comprises strips 22a and 22b of "Velcro" on the exterior surfaces respectively of the wall members 12 and 14.

The lower panel wall 14 is also preferably provided with another Velcro strip 24a which cooperates with a mating strip 24b (see FIG. 2) fixed to the support surface 26 of a stretcher. This arrangement provides an effective and easily releasable way of locating and holding the apparatus on the stretcher.

In the embodiment herein shown, the lower panel wall 14 is further provided with a conventional valve 28 of the type which is normally closed, and which opens in response to the attainment of a predetermined gas pressure in the chamber 16 to bleed gas therefrom and thus prevent the chamber from being over-pressurized. It will be understood that the type and location of the valve 28 is not critical, and that in fact the valve may be located anywhere where it is in communication with the chamber 16.

The embodiment herein disclosed further includes a flexible generally Y-shaped tube or conduit 30 having a pair of legs 32 connected to the lower sections 18a and 18b of the panel 11 and in communication as at 34 (see FIG. 3) with the chamber 16. The legs 32 are joined as at 36 and terminate in an end 38 which is adapted to be removably connected to another flexible tube or conduit 40 leading to a foot-operated air pump 42 of conventional design. The legs 32 also each include manually adjustable ON-OFF valves 44.

The apparatus is employed in the following manner: the panel 11 in a deflated condition, is laid out on any conveniently available surface, for example the support surface 26 of a stretcher as shown in FIG. 2. If desired, the mating Velcro strips 24a and 24b may be employed to locate the panel. At this stage, the lower sections 18a and 18b are open, with the former overlapping the latter, and the upper section 18c is also open. The victim is then laid on the panel 11, with the upper edge 20 of the upper section located just below the victim's rib cage. The victim's left leg is then wrapped with lower section 18a, with the Velcro strips 22a and 22b being employed to hold the section 18a in its applied position. In a like manner, the other lower section 18b is applied to the victim's right leg, and the upper section is applied to the victim's abdomen. The tube 40 is then connected to the end 38 of the Y-shaped conduit 30, and the pump 42 is employed to inflate the panel by introducing pressurized air into the chamber 16. Inflation continues until air begins to bleed out of valve 28, at which point the valves 44 are closed and the pump 42 disconnected. The victim is now ready for transport to a medical facility.

The pressure exerted on the victim's legs and abdomen by the inflated panel 11 mobilizes the blood pooled in these areas and increases venous return to the heart. This external pressure also provides immobilization for the victim and affords to him protection and comfort while being transported to a medical facility. These advantages are achieved in a simple, rapid and convenient manner not heretofore available to paramedical personnel, thereby making possible a significant improvement in the treatment of traumatized victims.

When the victim reaches his destination, or if it is necessary to gain access to a wound while the victim is in transit, the apparatus can be opened quickly by simply opening valves 44 to deflate the panel 11 and thereafter rapidly disengaging the Velcro fasteners 22a and 22b.

In light of the foregoing, it will now be evident to those skilled in the art that numerous changes may be made to the embodiment herein disclosed without departing from the spirit and scope of the invention. For example, the Velcro fastening strips 22a and 22b may be replaced by other conventional fastening devices, such as buckles, straps, laces, etc. The chamber 16 may be subdivided into several compartments, each of which may be pressurized individually. The pump 42 may be replaced by a pre-charged gas bottle or tank, which may be connected in any convenient manner and at any convenient location to the panel 11.

It is my intention to cover these and any other changes or modifications which are within the scope of the claims appended hereto.

We claim:

1. Apparatus for transferring pooled venous blood in the lower extremities and abdominal area of a victim suffering from shock, said apparatus comprising: a doublewalled panel of flexible material forming chamber means, said panel having a pair of lower sections adapted to operatively surround the legs of the victim and an upper section adapted to operatively surround the abdomen of the victim in the region below the victim's rib cage; fastening means on the exterior surface of said panel for retaining said sections in their operative positions on the victim; gas pressurizing means adapted to be placed in communication with said chamber means for inflating said panel to thereby exert pressure on the legs and abdomen of the victim in order to decrease the volume of venous blood pooled therein and thus increase venous return to the victim's heart; and normally closed valve means communicating with said chamber means and being operative to open in response to the attainment of a selected level of gas pressure in said chamber means to bleed gas from said chamber means.

2. The apparatus as claimed in claim 1 wherein said pressurizing means includes a source of pressurized gas removably connected to one end of a flexible conduit means, the other end of said conduit means being connected to said panel and in communication with said chamber means.

3. The apparatus as claimed in claim 2 wherein said source of pressurized gas comprises a manually operable air pump.

4. The apparatus as claimed in claim 2 further characterized by valve means in said conduit means between said chamber means and said source of pressurized gas, said valve means being manually adjustable between open and closed positions.

5. Apparatus for transfusing pooled venous blood in the lower extremities and abdominal area of a victim suffering from shock, said apparatus comprising: a double-walled panel of flexible material forming a chamber, said panel having a pair of lower sections adapted to operatively surround the legs of the victim, and an upper section adapted to operatively surround the abdomen of the victim in the region below the victim's rib cage; fastening means on the exterior surfaces of said panel for retaining said sections in their operative positions on the victim; conduit means connected to said panel and in communication at one end with said chamber; first valve means in said conduit means, said first valve means being manually adjustable between open and closed positions; normally closed second valve means in one of the walls of said panel, said second valve means being in communication with said chamber and being operative to open in response to the attainment of a predetermined gas pressure in said chamber; and pressurizing means removably connected to the other end of said conduit means, said pressurizing means being operable when said first valve means is open to introduce a gas through said conduit means into said chamber, thereby inflating said panel to exert pressure on the legs and abdomen of the victim in order to decrease the volume of venous blood pooled therein and thus increase venous return to the victim's heart.

* * * * *